United States Patent [19]

Kawai et al.

[11] Patent Number: 4,968,852

[45] Date of Patent: Nov. 6, 1990

[54] TRIFLUOROMETHYLBENZOYL BROMIDE AND CONVERSION OF SAME TO BROMOBENZOTRIFLUORIDE

[75] Inventors: Toshikazu Kawai, Kawagoe; Hideki Oshio, Omiya, both of Japan

[73] Assignee: Central Glass Company, Limited, Ube, Japan

[21] Appl. No.: 456,086

[22] Filed: Dec. 28, 1989

Related U.S. Application Data

[60] Continuation of Ser. No. 244,593, Sep. 13, 1988, abandoned, which is a division of Ser. No. 30,616, Mar. 27, 1987.

[30] Foreign Application Priority Data

Apr. 1, 1986 [JP] Japan .................... 61-72413
Jun. 9, 1986 [JP] Japan .................... 61-131937

[51] Int. Cl.$^5$ .................................. C07C 17/00
[52] U.S. Cl. ............................ 570/142; 570/127; 562/861; 562/863
[58] Field of Search ............ 570/142, 127; 562/861, 562/863

[56] References Cited

U.S. PATENT DOCUMENTS 2,704,776  3/1955  La Zerte et al. .
4,500,471  2/1985  Cotter et al. .
4,581,179  4/1986  Tang et al. .

OTHER PUBLICATIONS

Tsuji et al., J.A.C.S., 90 (1) (1968), pp. 94–98.
Wegand et al., Preparative Organic Chemistry, John Wiley, New York, (1972), pp. 243, 246 & 247, 249.
"Photochemical Bromination of Simple Arenes", by Roger Bolton et al., J. Chem. Soc. Perkin Trans. 1, 1984, pp. 893–896.
"A New Method for the Trifluoromethylation of Aromatics", by A. Marhold et al., Journal of Fluorine Chemistry, vol. 18, 1981, pp. 281–291.
Chemical Abstracts, vol. 83, 1975, 9118r, p. 758.

*Primary Examiner*—Howard T. Mars
*Attorney, Agent, or Firm*—Fleit, Jacobson, Cohn, Price, Holman & Stern

[57] ABSTRACT

A novel compound, trifluoromethylbenzoyl bromide, is formed by bromination of trifluoromethylbenzoic acid with, e.g., phosphorus tribromide or by halogen exchange reaction of trifluoromethylbenzoyl chloride with bromine in the presence of a metal bromide. Decarbonylation of 2-, 3- or 4-trifluoromethylbenozyl bromide using a catalyst such as a phosphine-rhodium complex gives 2-, 3- or 4-bromobenzotrifluoride without forming isomers.

5 Claims, No Drawings

TRIFLUOROMETHYLBENZOYL BROMIDE AND CONVERSION OF SAME TO BROMOBENZOTRIFLUORIDE

This application is a continuation, of application Ser. No. 97/244,593, filed Sept. 13, 1988, which is a divisional of application Ser. No. 097/030,616, filed Mar. 27, 1987, both abandoned.

BACKGROUND OF THE INVENTION

This invention relates to novel compounds, viz 2-, 3- and 4-trifluoromethylbenzoyl bromides, and a method of preparing the same and to a method of converting 2-, 3- or 4-trifluoromethylbenzoyl bomide to 2-, 3- or 4- bromobenzotrifluoride.

Bromobenzotrifluoride is of use as an intermediate material for some medicines and agricultural chemicals.

A known method for preparation of bromobenzotrifluoride is bromination of benzotrifluoride (J. Chem. Soc., P.T. 1 (1984), 893). However, the product of this method is always a mixture of three isomers, 2-, 3- and 4bromobenzotrifluorides. Another method is trifluoromethylation of bromobenzene (J. Fluorine Chem., Vol. 18 (1981), 281), but the product of this method is a mixture of 2- and 4-bromobenzotrifluorides. Still another method is fluorinating bromobenzoic acid with $SF_4$ (Chem. Abstr., Vol. 83 (1975), 9118r). By this method a desired product such as, for example, 2-bromobenzorifluoride from 2-bromobenzoic acid is obtained without forming unwanted isomers. However, this method is unsuitable for industrial application because of very high toxicity of $SF_4$.

SUMMARY OF THE INVENTION

It is an object of the present invention to provide an industrially practicable method of preparing 2-, 3- or 4-bromobenzotrifluoride without forming unwanted isomers.

It is another object of the invention to provide a novel compound from which bromobenzotrifluoride is easily obtained and a method of preparing the novel compound.

We have discovered that a novel compound, which is named trifluoromethylbenzoyl bromide and exists in three forms represented by the general formula (1), is formed by bromination of trifluoromethylbenzoic acid or by halogen exchange reaction of trifluoromethylbenzoyl chloride with bromine and that 2-, 3- or 4-bromobenzotrifluoride is obtained by decarbonylation of 2-, 3- or 4-trifluoromethylbenzoyl bromide.

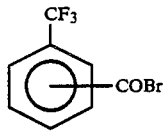

(1)

Accordingly, one aspect of the present invention is a novel compound. viz. trifluoromethylbenzoyl bromide, represented by the general formula (1). According to the invention, this novel compound is prepared by reacting 2-, 3- or 4-trifluoromethylbenzoic acid with a brominating agent or by reacting 2-, 3- or 4-trifluoromethylbenzoyl chloride with bromine in the presence of a metal bromide.

In another aspect of the invention, there is provided a method of preparing 2-, 3- or 4-bromobenzotrifluoride, comprising heating 2-, 3- or 4-trifluoromethylbenzoyl bromide in the presence of a decarbonylation catalyst.

The novel compound, trifluoromethylbenzoyl bromide, is useful as a raw material of intermediates of some medicines, agricultural chemicals or liquid crystals.

Both of trifluoromethylbenzoic acid and trifluoromethylbenzoyl chloride alternatively employed as the starting material in this invention are readily available industrial materials, and the brominating agents for use in this invention are also industrially available and handlable materials. The reactions which are utilized in this invention proceed under relatively mild conditions.

Another important advantage of the invention resides in that any of 2-, 3- and 4-bromobenzotrifluorides can be obtained with good yield and without coexistence of isomers.

DETAILED DESCRIPTION OF THE INVENTION

For bromination of 2-, 3- or 4-trifluoromethylbenzoic acid, this invention employs an inorganic or organic bromide as the brominating agent. It is suitable to use phosphorus tribromide, phosphorus pentabromide, thionyl bromide, sulfuryl bromide, oxalyl bromide or triphenylphosphine dibromide. The amount of the brominating agent should be somewhat in excess of the stoichiometric quantity. The brominating reaction temperature is variable depending on the kind of the brominating agent and, in general, ranges from room temperature to about 200° C. The reaction is completed in 1–10 hr.

In the case of subjecting trifluoromethylbenzoyl chloride to halogen exchange reaction with bromine in the presence of a metal bromide, it is suitable to select the bromide from alkali metal bromides represented by sodium bromide and potassium bromide or from alkaline earth metal bromides. In this case the principal brominating agent is bromine. Therefore, at least a stoichiometric quantity of bromine is used. The amount of the metal bromide is variable and ranges from a catalytic quantity to a quantity approximately equivalent to the principal brominating agent. The reaction temperature ranges from room temperature to about 100° C., and the reaction time is 2–20 hr.

Decarbonylation of 2-, 3- or 4-trifluoromethylbenzoyl bromide to obtain 2-, 3- or 4-bomobenzotrifluoride is accomplished by using a decarbonylation catalyst. Effective catalysts can be found among rhodium compounds, palladium compounds and ruthenium compounds. It is preferred to use rhodium, palladium or ruthenium in the form of a metal complex, such as tris-triphenylphosphinerhodium chloride, tris-triphenylphosphinerhodium bromide or bis-triphenylphosphinepalladium dichloride. The amount of the decarbonylation catalyst is at least 0.01 mol%, and preferably not less than 0.1 mol%, of trifluoromethylbenzoyl bromide to be decarbonylated. It is suitable to carry out the decarbonylation reaction at a temperature in the range from about 150° C. to about 250° C.

The invention is further illustrated by the following nonlimitative examples.

EXAMPLE 1

In a 300 ml glass reactor, 190 g of 2-trifluoromethylbenzoic acid was reacted with 160 g of phosphorus tribromide at 170° C. for 2 hr. After that the reaction liquid was distilled to first remove unreacted phosphorus tribromide and then obtain 2-trifluoromethylbenzoyl bromide having a boiling point of 210.8° C. This reaction product weighed 186 g, meaning that the yield was 74%.

On this reaction product, NMR spectrometry and mass spectrometry (MASS) gave the following data.
$^{19}$F-NMR (standard: CF$_3$CO$_2$H) in CCl$_4$:
−17.1 ppm (3F, s).
$^1$H-NMR (standard: TMS) in CCl$_4$:
7.6–8.0 ppm (4H, m).
MASS, m/e values: 173 (M$^+$—Br), 145 (M$^+$—COBr).

Next, decarbonylation of 2-trifluoromethylbenzoyl bromide was carried out. Initially 2 g of tris-triphenylphosphinerhodium chloride (decarbonylation catalyst) was charged in a 30 ml Cleisen flask and heated to 210° C., and, maintaining that temperature, 169 g of 2-trifluoromethylbenzoyl bromide was slowly introduced into the flask, while collecting the distillate. In this case the amount of the catalyst was 0.32 mol% of the bromide. The total quantity of the collected distillate was 132 g. By distillating this liquid, 110 g of 99.8% purity 2-bromobenzotrifluoride was obtained. The yield in this reaction was 77%.

EXAMPLE 2

In a sealed tube, 1 g of 2-trifluoromethylbenzoyl bromide prepared in Example 1 was heated at 240° C. for 1.5 hr together with 0.02 g (0.55 mol%) of tris-triphenylphosphinerhodium chloride. After that the reaction liquid was analyzed by gas chromatography. The analysis revealed that the conversion of 2-trifluoromethylbenzoyl bromide had reached 98.0%, that selectivity to 2-bromobenzotrifluoride was 99.0% and that no isomer was present in a detectable quantity.

EXAMPLE 3

In a 50 ml glass reactor, 30 g of 4-trifluoromethylbenzoic acid and 14.5 g of phosphorus tribromide were reacted at 155° C. for 3 hr. After that the reaction liquid was distilled under reduced pressure to obtain 23 g of 4-trifluoromethylbenzoyl bromide having a boiling point of 88°–89° C. at 18 mmHg. The yield in this reaction was 58%.

NMR and MASS analysis of this reaction product gave the following data.
$^{19}$F-NMR (standard: CF$_3$CO$_2$H) in CCl$_4$: −14.0 ppm (3F, s).
$^1$H-NMR (standard: TMS) in CCl$_4$: 8.0 ppm (2H, d), 7.6 ppm (2H, d).
MASS, m/e values: 173 (M$^+$—Br), 145 (M$^+$—COBr).

To carry out decarbonylation reaction, 1 g of 4-trifluoromethylbenzoyl bromide was heated in a sealed tube together with 0.01 g (0.27 mol%) of tris-triphenylphosphinerhodium chloride at 250° C. for 1.5 hr. After that gas chromatography analysis of the reaction liquid revealed that the conversion of the starting bromide had reached 98.9% and that selectivity to 4-bromobenzotrifluoride was 99.3%.

EXAMPLE 4

Bromination of 3-trifluoromethylbenzoic acid was performed by substantially the same method as in Example 3. As the result, 21 g of 3-trifluoromethylbenzoyl bromide was obtained from 30 g of the starting material. The yield was 53%.

The boiling point of the obtained bromide was 86°–88° C. at 17–18 mmHg. NMR and MASS analysis of this bromide gave the following data.
$^{19}$F-NMR (standard: CF$_3$CO$_2$H) in CCl$_4$: −13.6 ppm (3F, s).
$^1$H-NMR (standard: TMS) in CCl$_4$: 7.5–8.3 ppm (4H, m).
MASS, m/e values: 173 (M$^+$—Br), 145 (M$^+$—COBr).

Next, 1 g of 3-trifluoromethylbenzoyl bromide was subjected to decarbonylation reaction in the same manner as in Example 3. In this case the conversion of the starting bromide reached 100% within 1.5 hr, and selectivity to 3-bromobenzotrifluoride was 99.6%.

EXAMPLE 5

In a 20 ml glass reactor, 10.4 g of 2-trifluoromethylbenzoyl chloride, 3.0 g of sodium bromide and 8.0 g of bromine were reacted at 50° C. for 10 hr. After that, unreacted bromine was purged from the reactor by using nitrogen gas, and solid matter was removed from the reaction system by filtration. Gas chromatography analysis of the reaction liquid revealed that 52% of 2-trifluoromethylbenzoyl chloride had converted to 2-trifluoromethylbenzoyl bromide. By fractional distillation of the reaction liquid, 5.9 9 of 2-trifluoromethylbenzoyl bromide having a boiling point of 210.8° C. was obtained. NMR and MASS analysis of this bromide gave the following data.
$^{19}$F-NMR (standard: CF$_3$CO$_2$H) in CCl$_4$: −17.1 ppm (3F, s).
$^1$H-NMR (standard: TMS) in CCl$_4$: 7.6–8.0 ppm (4H, m).
MASS, m/e values: 173 (M$^+$—Br), 145 (M$^+$—COBr).

To carry out decarbonylation reaction, 5.9 g of 2-trifluoromethylbenzoyl bromide was heated in a sealed tube together with 0.06 g of tris-triphenylphosphinerhodium bromide at 220° C. for 2.5 hr. After that gas chromatography analysis of the reaction liquid revealed that the conversion of 2-trifluoromethylbenzoyl bromide had reached 100% and that selectivity to 2-bromobenzotrifluoride was 100%.

What is the claimed is
1. A method of preparing bromobenzotrifluoride, comprising the steps of:
   (a) reacting trifluoromethylbenzoic acid with a brominating agent to produce trifluoromethylbenzoyl bromide; and the
   (b) decarbonylating said trifluoromethylbenzoyl bromide by heating said trifluoromethylbenzoyl bromide in the presence of a decarbonylation catalyst at a temperature in the range of from about 150° C. to about 250° C. to produce bromobenzotrifluoride, said decarbonylation catalyst being a rhodium complex.
2. A method according to claim 1, wherein said rhodium complex is selected from the group consisting of tris-triphenylphosphinerhodium chloride and tris-triphenylphosphinerhodium bromide.
3. A method according to claim 1, wherein said brominating agent is a bromide selected from the group consisting of phosphorus tribromide, phosphorus pentabromide, thionyl bromide and sulfuryl bromide.
4. A method according to claim 1, wherein said brominating agent is an organic bromide selected from the group consisting of oxalyl bromide and triphenylphosphine dibromide.
5. A method according to claim 1, wherein the reaction is carried out at a temperature in the range from room temperature to about 200° C.

* * * * *